(12) United States Patent
Smith, III

(10) Patent No.: US 11,033,416 B1
(45) Date of Patent: Jun. 15, 2021

(54) BACK SUPPORT DEVICE

(71) Applicant: Ray H. Smith, III, Dewey, AZ (US)

(72) Inventor: Ray H. Smith, III, Dewey, AZ (US)

( * ) Notice: Subject to any disclaimer, the term of this patent is extended or adjusted under 35 U.S.C. 154(b) by 0 days.

(21) Appl. No.: 16/539,516

(22) Filed: Aug. 13, 2019

Related U.S. Application Data

(60) Provisional application No. 62/718,175, filed on Aug. 13, 2018.

(51) Int. Cl.
*A61F 5/02* (2006.01)
*A41D 13/05* (2006.01)

(52) U.S. Cl.
CPC .......... *A61F 5/028* (2013.01); *A41D 13/0531* (2013.01); *A41D 2400/32* (2013.01)

(58) Field of Classification Search
CPC .. A61F 5/01; A61F 5/022; A61F 5/024; A61F 5/028; A61F 5/03; A61F 2007/0024; A61F 2007/0027; A61F 5/02–03; A41D 13/0515; A41D 13/0525; A41D 13/0531; A41D 2400/32; A41D 2400/322; A41D 13/05–088; A45F 5/021; A45F 5/02; A45F 5/00; A45F 5/022; F41C 33/041; F41C 33/04–045; F41C 33/02; Y10S 224/904; Y10S 224/914; Y10S 224/931; Y10S 224/911; A63B 71/08; A63B 71/10–148
USPC ....... 602/19; 2/467; 224/666, 667, 668, 669, 224/182, 255, 256, 673
See application file for complete search history.

(56) References Cited

U.S. PATENT DOCUMENTS

| | | | | |
|---|---|---|---|---|
| 3,937,373 | A * | 2/1976 | Artz | A45F 5/02 224/666 |
| 4,572,167 | A * | 2/1986 | Brunswick | A61F 5/028 2/44 |
| 4,784,199 | A * | 11/1988 | Wise | A45C 1/08 150/134 |
| 4,821,934 | A * | 4/1989 | Alessi | A45F 5/02 224/667 |
| 4,991,573 | A * | 2/1991 | Miller | A61F 5/028 128/106.1 |
| 5,188,585 | A * | 2/1993 | Peters | A61F 5/028 128/100.1 |
| 5,983,407 | A * | 11/1999 | McKay | A41D 13/0531 2/231 |
| 6,108,819 | A | 8/2000 | DeBaene et al. | |

(Continued)

OTHER PUBLICATIONS

DR-HO'S 2-in-1 Back Decompression Belt Basic. Datasheet [online]. VGH Solutions Inc., 2019 [retrieved on Jul. 25, 2019]. Retrieved from the Internet: <URL: https://drhonow.com/en_us/2-in-1-back-decompression-belt-basic-package/?gclid=CjwKCAjwpuXpBRAAEiwAyRRPgXlxeDa-Vzhu_COAR3yFsttRgX68yqL3Mbnyd-Nuoxz_co8zhLriQRoCnVEQAvD_BwE>.

*Primary Examiner* — Keri J Nelson
*Assistant Examiner* — Michelle J Lee
(74) *Attorney, Agent, or Firm* — Cramer Patent & Design, PLLC; Aaron R. Cramer

(57) ABSTRACT

A back support device includes a plurality of durable and semi-rigid layers. One of the layers is capable of conforming to the contours of a body part of user. At least one clip enables the device to be supported on a lower garment worn by the user. The back support device more specifically includes a first layer, a second layer, a third layer, an insert disposed between the second layer and the third layer, a pair of slits disposed on the first layer, on the second layer, and (Continued)

on the third layer, and a pair of clips respectively inserted through each the pair of slits.

8 Claims, 4 Drawing Sheets

(56) References Cited

U.S. PATENT DOCUMENTS

| | | | |
|---|---|---|---|
| 6,398,092 B1* | 6/2002 | Ansley | A45F 5/02 |
| | | | 224/582 |
| D749,230 S | 2/2016 | Safko et al. | |
| 10,052,223 B2 | 8/2018 | Turner | |
| 10,159,592 B2 | 12/2018 | Ingimundarson et al. | |
| 2010/0318011 A1* | 12/2010 | Hirota | A61F 5/028 |
| | | | 602/19 |
| 2016/0029777 A1* | 2/2016 | Gadams | A45F 5/00 |
| | | | 224/222 |
| 2017/0340472 A1 | 11/2017 | Turner | |

* cited by examiner

BACK SUPPORT DEVICE

RELATED APPLICATIONS

This application claims the benefit of U.S. Provisional Application No. 62/718,175, which was filed Aug. 13, 2018, the entire disclosures of which are incorporated herein by reference.

FIELD OF THE INVENTION

The present invention relates generally to a back support device and more specifically to a back support device configured to be worn by user about the upper top rear portion of a pair of pants of the user.

BACKGROUND OF THE INVENTION

There is a great deal of people who suffer from back pain that is derived from a number of sources. Many people suffer from residual pain that began as a result of a previous injury or surgery that never completely heals or is easily aggravated. Others suffer from pain that stems from an aggregation of years of improper posturing and insufficient exercise practices. Regardless of its origin, there are many methods to help reduce this pain and increase comfort.

One of the most popular methods is that of wearing of a back brace. However, even though these braces are somewhat adjustable for the individual user, they are not customized to the exact shape of the user's back. This means that they remain uncomfortable and constrict the wearer's back from complete range of motion. As such, they do not allow the wearer to move and perform job functions and even reduce quality of living. Accordingly, there exists a need for a means by which a back-pain sufferers can be provided with relief in a method that addresses the above-mentioned concerns. The development of the Back Support Device fulfills this need.

SUMMARY OF THE INVENTION

The principles of the present invention provide for a back support device comprising a first layer, a second layer, a third layer, an insert disposed between the second layer and the third layer, a pair of slits disposed through the third layer and a pair of clips respectively disposed through each the pair of slits. The first layer, the second layer, the third layer and the insert are secured together forming a unitary structure. Each of the pair of clips have a clip end which project outward from a first face of the third layer each forming an open clip end. Each the open clip end is configured to removably secure over the top rear edge of a pair of pants worn by a user. When secured over the top rear edge of a pair of pants worn by a user, the back support device provides semi-flexible support for a lower back of the user.

The pair of slits may be disposed within the third layer along a common bisecting horizontal centerline, may be disposed equidistantly along the common bisecting horizontal centerline and may be disposed subjacent a first lengthwise edge of the third layer. The first layer, second layer, third layer and insert each may be generally rectangular. Each of the pair of clips may be secured to a second face of the third layer by a corresponding pair of fasteners.

Each of the pair of clips may individually comprise an elongated first portion, a curvilinear bent middle portion and a second portion which terminates in the open clip end that is bent outwards relative to the first portion. The insert may comprise a resilient and flexible material capable of conforming its shape to that of the lower back of the user. The resilient and flexible material may comprise a thermoplastic acrylic-polyvinyl chloride material or KYDEX®. The first layer, the second layer, the third layer and the insert may be secured together forming a unitary structure using an adhesive. The first layer and the third layer may further be secured by means of stitching about the peripheral edge of the first layer and the third layer. The corresponding pair of fasteners may comprise a corresponding rivet. The insert may freely reside between the second layer and the third layer. The first layer, second layer and third layer may comprise leather. Each of the pair of clips may comprise spring steel.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
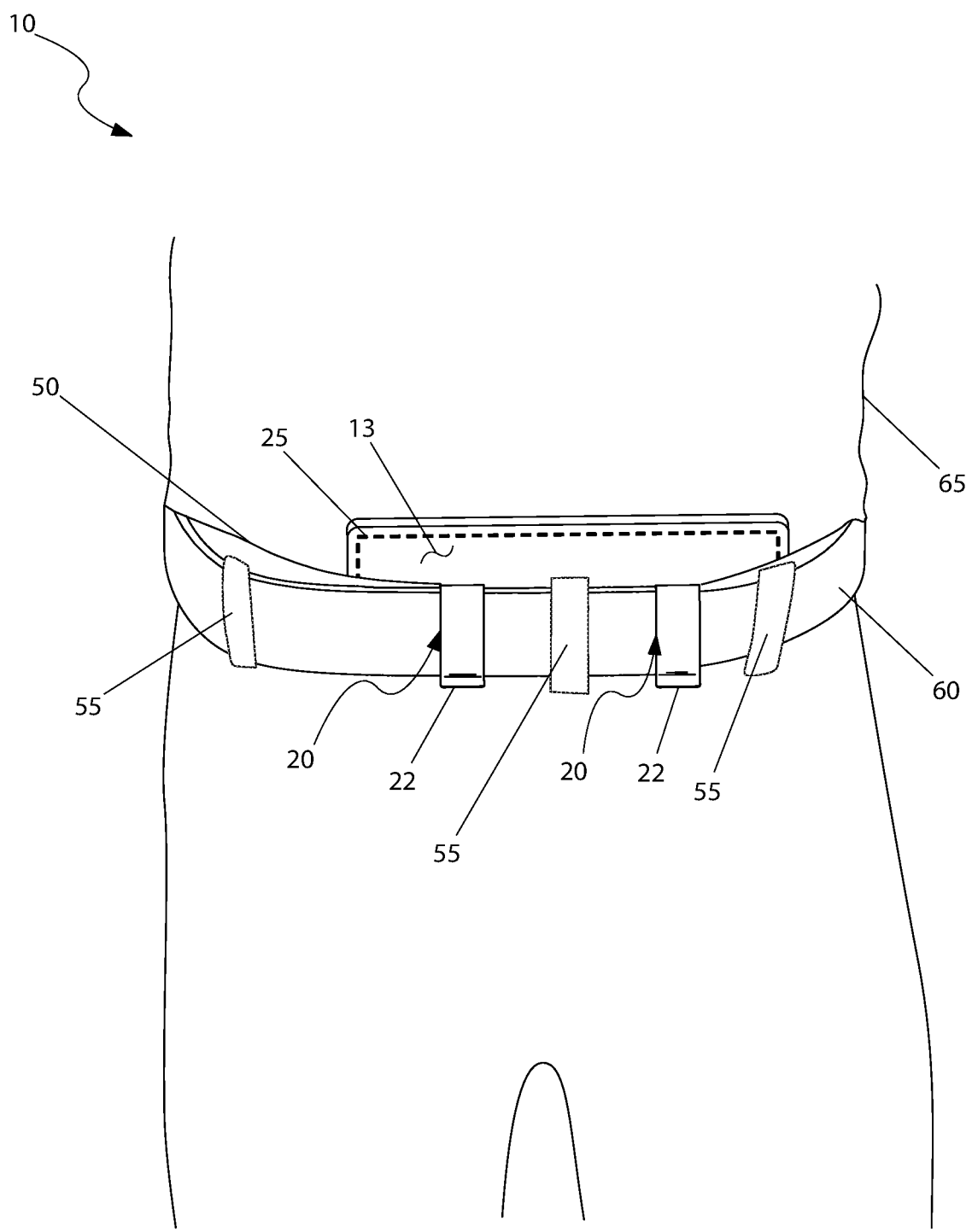
FIG. 1 is an environmental view of aback support device 10 as worn by a user 65, according to a preferred embodiment of the present invention.
Figure 2:
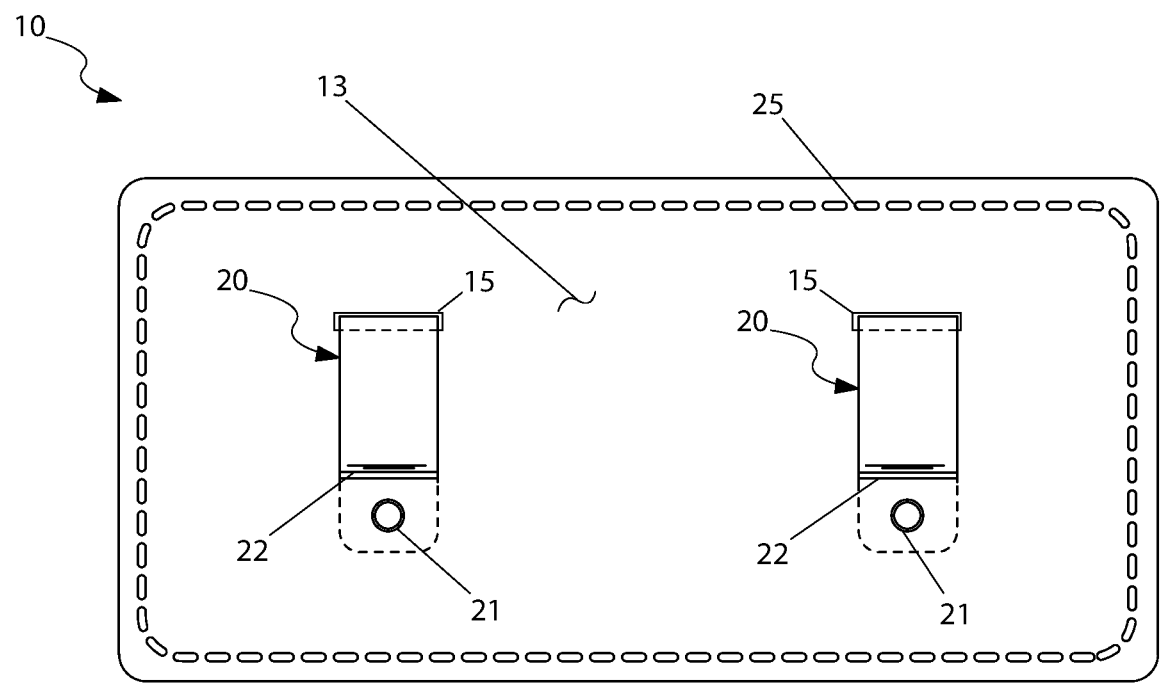
FIG. 2 is a front side elevation view of the back support device 10, according to the preferred embodiment of the present invention.
Figure 3:
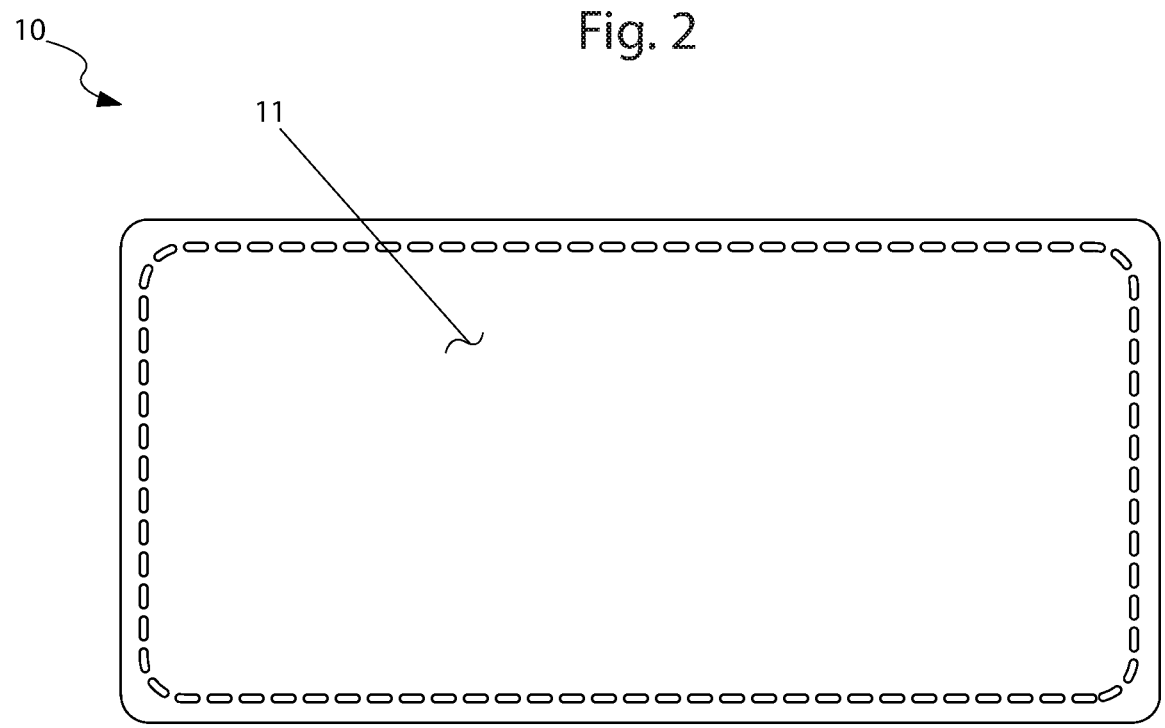
FIG. 3 is a rear side elevation view of the back support device 10, according to the preferred embodiment of the present invention.
Figure 4:
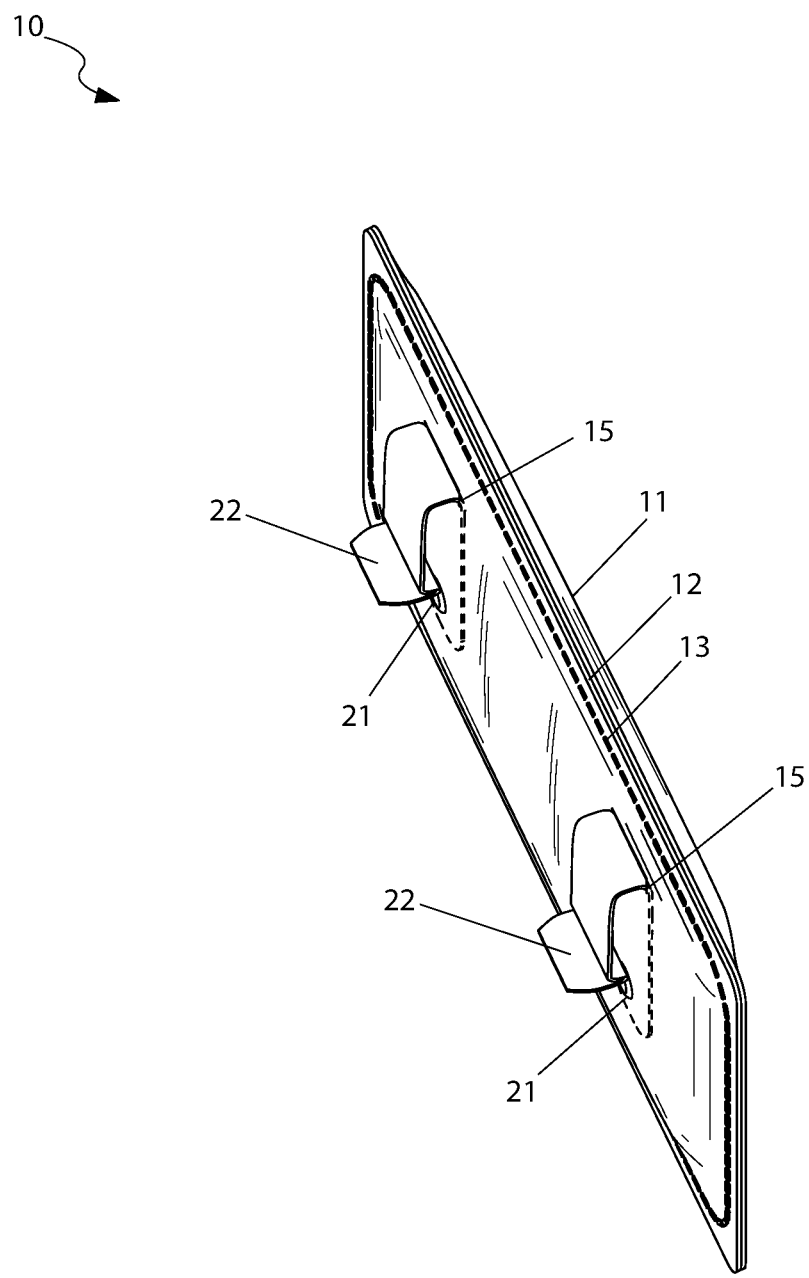
FIG. 4 is a top perspective view of the back support device 10, according to the preferred embodiment of the present invention; and, FIG. 5 is an exploded perspective view of the back support device 10, according to the preferred embodiment of the present invention.

DESCRIPTIVE KEY 10 back support device
11 first layer
12 second layer
13 third layer
15 slit
20 clip
21 fastener
22 clip end
25 stitching
30 insert
50 lower garment
55 belt loop
60 belt
65 user

DESCRIPTION OF THE PREFERRED EMBODIMENTS

The best mode for carrying out the invention is presented in terms of its preferred embodiment, herein depicted within FIGS. 1 through 5. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims.

The terms "a" and "an" herein do not denote a limitation of quantity, but rather denote the presence of at least one (1) of the referenced items.

1. DETAILED DESCRIPTION OF THE FIGURES

Referring now to FIGS. 2-5, various views of a back support device (herein described as the "device) is herein described. The device 10 is particularly suited for users 65 who have seen a need to have support placed on their back but do not wish to have to bulky and constricting apparatuses used. Generally, the device 10 incorporates a first layer 11, a second layer 12, an insert 30, a third layer 13, and at least one (1) clip 20.

Figure 5:
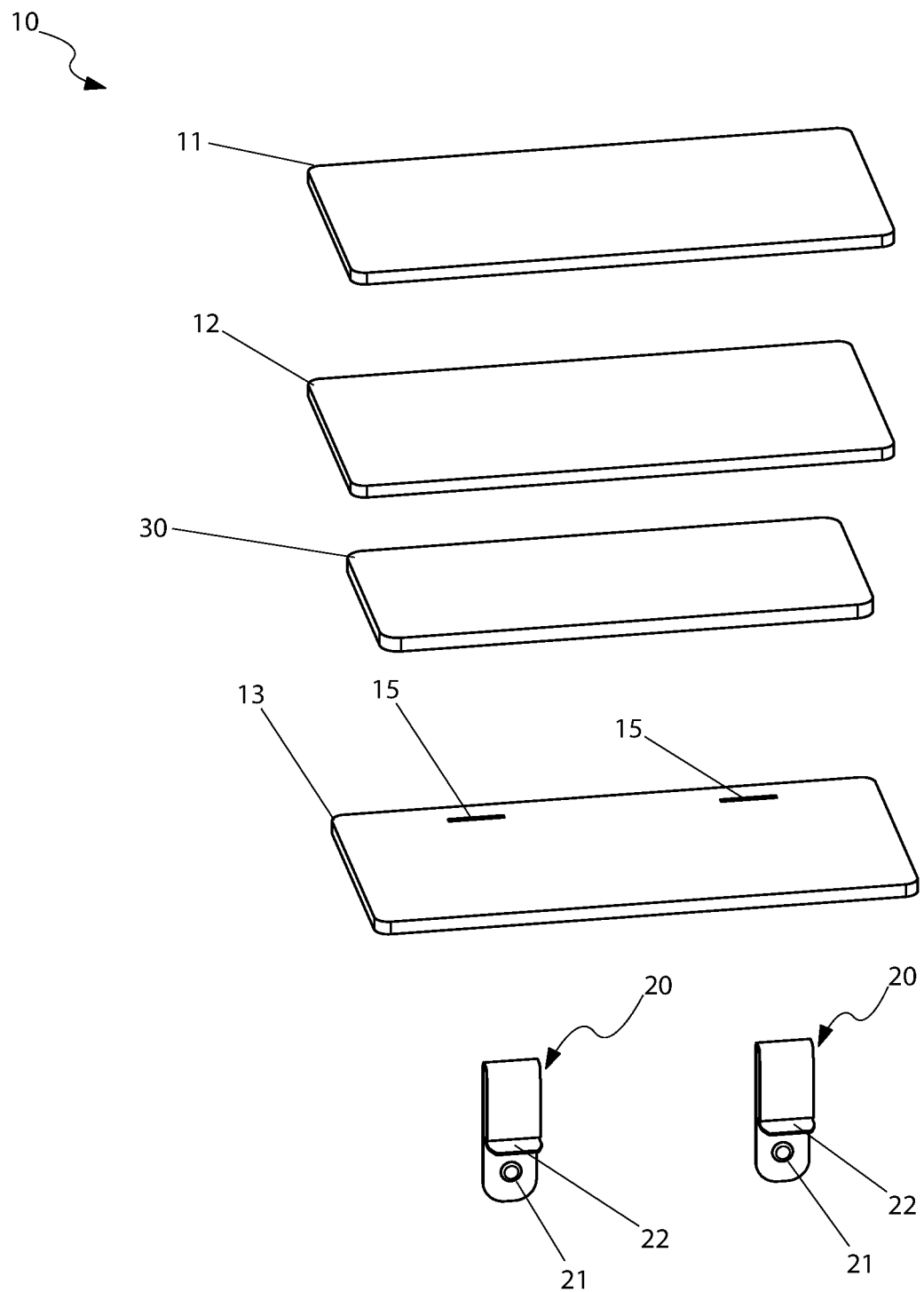

Referring more closely now to FIG. 5, there is shown the device 10 in an exploded view to illustrate the disparate elements. A first layer 11, a second layer 12, and a third layer 13 are each preferably identical in material and shape and are expected to have perimeters that are coextensive with each other. In a preferred embodiment, the first, second, and third layers 11, 12, 13 are a leather or other similar material noted for relative flexibility, resiliency, and conformity. The thickness of the layers 11, 12, 13 may be identical, or varying. In a preferred embodiment, the layers 11, 12, 13 are rectangular in shape and have a pair of long sides and a pair of short sides. When worn by a user 65 (as is illustrated in FIG. 1), the long sides are rendered parallel with the waist of the user 65. In an exemplary embodiment, the corners are rounded.

The third layer 13 also incorporates a pair of slits 15 that are preferably aligned along a common bisecting horizontal centerline and also preferably each equidistant from a common vertical bisecting centerline. The slits 15 are located closer towards one (1) of the long sides. A clip 20 is capable of being inserted into an individual slit 15 as fastened thereto with a fastener 21. An exemplary embodiment of such a clip 20 can entail a spring steel having an elongated first portion that is capable of being inserted into the slit 15, a curvilinear bent middle portion, and a second portion that is parallel with the first end and terminates with a clip end 22 that is bent outwards relative to the first portion. The clip end 22 terminates at a length shorter than the terminal end of the first portion. The fastener 21 secures the outer side of the third layer 13 with the first portion of the clip that resides on the inner side of the third layer 13. The second portion of the clip 20 is biased towards the outer side of the third layer 13 and the first portion of the clip 20 when the clip 20 is fastened to the third layer 13. An outward force applied to the clip end 22 enables deflection of the second portion away from the outer side of the third layer 13 temporarily. Although the exemplary embodiment describes two (2) clips, it is appreciated that any number of clips 20 and slits 15 can be utilized and function in the prescribed manner.

The insert 30 is manufactured out of a resilient and flexible material that is capable of conforming to the user 65 when worn. Most preferably, the insert 30 is initially provided as a basic rigid shape and, more specifically related to the current device 10, available in a rectangular shape with rounded corners having a perimeter size slightly smaller overall than the perimeter sizes of the first, second, and third layers 11, 12, 13. When gently heated, the material can experience relative flexibility that enables it to conform to the contours of the user 65. When the insert 30 is subsequently cooled, the material maintains the shape of the contour it conforms to. In a preferred embodiment, the material is a thermoplastic acrylic-polyvinyl chloride material or KYDEX®.

In a preferred method of construction, the first layer 11 and second layer 12 are bonded together, preferably with an adhesive, such that the perimeters thereof are coextensive. The insert 30 is bonded in a similar fashion to the center of the second layer 12 opposite the first layer 11. The first portion of an individual clip 20 is inserted into a slit 15 of the third layer 13, such that the second portion and the clip end 22 remain on the opposite side thereof. A fastener 21, such as a rivet, secures the clip 20 to the third layer 13. The third layer 13 with all clips 20 secured thereto is bonded to the second layer 12 opposite the first layer 11, such that the insert 30 is centered therein. Stitching 25 is then applied to the device 10 to bond the first layer 11 to the third layer 13.

Alternately, the insert 30 can be bonded to the third layer 13 in the same fashion as it is bonded to the second layer 12, or the insert 30 can freely reside between the second layer 12 and third layer 13 without any bonding.

In a preferred method of use, such as that illustrated in FIG. 1, the device 10 is inserted in the inside of a lower garment 50 such as a pair of pants, and the first layer 11 abuts a body part of the user 65, such as the lower back. The clip end 22 of each clip 20 is forced outward to enable the curvilinear portion of the clip 20 to retain a portion of the upper perimeter edge of the lower garment 50. The clip end 22 is then released and the clip 20 secures the device to the lower garment 50. In certain embodiments, the lower garment 50 may be secured to the user 65 with a belt 60 routed through a plurality of belt loops 55. Each clip 50 therefore can retain a portion of the belt 60 as well. The latent heat of the user 65 then gently warms the insert 30, which then conforms to the contour of the body part of the user 65.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

The invention claimed is:

1. A back support device, comprising: a first layer; a second layer; a third layer; an insert disposed between said second layer and said third layer; a pair of slits made in said third layer and disposed on said first layer and said second layer; and a pair of clips, each clip inserted through a respective slit of said pair of slits; wherein said first layer, said second layer, said third layer and said insert are secured together forming a unitary structure; wherein each clip of said pair of clips has a clip end which projects outward from a first face of said third layer to form an open clip end; wherein each said open clip end is removably secured over a top rear edge of a pair of pants configured to be worn by a user; wherein when secured over said top rear edge of said pair of pants worn by said user, said back support device is adapted to conform its shape to that of a lower back of said user; wherein each clip of said pair of clips is secured to a second face of said third layer by a respective fastener of a pair of fasteners; wherein said insert is made of a resilient and flexible material adapted to conform its shape to that of said lower back of said user; wherein each clip of said pair of clips includes an elongated first portion, a curvilinear bent middle portion, and a second portion which terminates in said open clip end that is bent outwards relative to said first portion; wherein said third layer is generally rectangular; wherein said third layer is made of leather; wherein said first layer, said second layer, said third layer and said insert are secured together into the unitary structure using an adhesive; wherein said first layer and said third layer are further secured by stitching about a peripheral edge of said first layer and said third layer; and wherein each clip of said pair of clips is made of spring steel.

2. The back support device of claim 1, wherein said first layer is generally rectangular.

3. The back support device of claim 1, wherein said second layer is generally rectangular.

4. The back support device of claim 1, wherein said insert is generally rectangular.

5. The back support device of claim 1, wherein said resilient and flexible material is made of a thermoplastic acrylic-polyvinyl chloride material.

6. The back support device of claim 1, wherein each one of said pair of fasteners include a corresponding rivet for each fastener of said pair of fasteners.

7. The back support device of claim 1, wherein said first layer is made of leather.

8. The back support device of claim 1, wherein said second layer is made of leather.

* * * * *